United States Patent [19]

Schönafinger et al.

[11] Patent Number: 5,554,611
[45] Date of Patent: Sep. 10, 1996

[54] USE OF COUMARIN DERIVATIVES

[75] Inventors: Karl Schönafinger, Alzenau; Peter Klemm, Bretzenheim; Jörg Ostrowski, deceased, late of Rodenbach, all of Germany, by Thomas Ostrowski and Stefanie Ostrowski, legal representatives

[73] Assignee: Cassella Aktiengesellschaft, Frankfurt am Main, Germany

[21] Appl. No.: 336,374

[22] Filed: Nov. 8, 1994

[30] Foreign Application Priority Data

Nov. 8, 1993 [DE] Germany ............... 43 37 906.0

[51] Int. Cl.$^6$ .............. A61K 31/54; A61K 31/535; A61K 31/495; A61K 31/445
[52] U.S. Cl. ............. 514/228.2; 514/233.5; 514/255; 514/318; 514/320; 514/337; 514/385; 514/422; 514/457
[58] Field of Search .......... 514/228.2, 233.5, 514/255, 318, 320, 337, 385, 422, 457

[56] References Cited

U.S. PATENT DOCUMENTS

| | | | |
|---|---|---|---|
| 3,515,721 | 6/1970 | Ritter et al. | 260/247.2 |
| 3,652,557 | 3/1972 | Beyerle et al. | 260/247.2 |
| 3,726,902 | 4/1973 | Beyerle et al. | 260/343.3 |
| 3,732,251 | 5/1973 | Beyerle et al. | 260/343.2 |
| 3,772,280 | 11/1973 | Beyerle et al. | 260/243 B |
| 3,897,419 | 7/1975 | Bender et al. | 260/240 |
| 3,959,281 | 5/1976 | Beyerle et al. | 260/268 |

FOREIGN PATENT DOCUMENTS

| | | |
|---|---|---|
| 1210883 | 8/1966 | Germany . |
| 1246754 | 2/1968 | Germany . |
| 1259349 | 8/1968 | Germany . |
| 1962154 | 6/1971 | Germany . |
| 1668877 | 10/1971 | Germany . |
| 2247691 | 4/1974 | Germany . |
| WO93/13055 | 7/1993 | WIPO . |

OTHER PUBLICATIONS

Spektrum der Wissenschaft, "Stickstoffmonoxid—Regulator biologischer Signale", Jul., 1992, pp. 72–80.
European Journal of Pharmacology, "Cloricromene, a coumarine derivative, etc." 210 (1992) pp. 107–113.
Database Medline Dialog, file 155, accession No. 05884770, Fiedler VB. et al. & Arch Int. Pharmacodyn. Ther., Bd. 279, Nr. 1, 1986; pp. 103–120.
Surgery Gynecology & Obstetrics, Bd. 143, Nr. 4, Oktober 1976 Peyton M. D. et al., pp. 533–538.

Primary Examiner—Kimberly Jordan
Attorney, Agent, or Firm—Perman & Green

[57] ABSTRACT

The present invention consequently relates to the use of coumarins of the general formula I

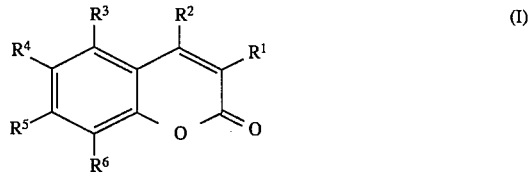

in which $R^1$ and $R^6$ are defined as indicated in the claims, for controlling and preventing disorders which arise as a result of an elevated NO level.

10 Claims, No Drawings

USE OF COUMARIN DERIVATIVES

The present invention relates to the use of couramin derivatives for controlling and preventing disorders which arise as a result of an elevated NO level.

Nitrogen monoxide (NO) plays an important role in a wide variety of physiological processes (see, for example, Spektrum der Wissenschaft (Spectrum of Science), July 1992, page 72). Thus, it is involved, for example, in the regulation of platelet function and of blood pressure, in immune defence, in cerebral functions such as learning and memorizing processes, and in inflammatory processes.

Endogenous nitrogen monoxide is formed from arginine with the aid of NO synthases. At least two such enzymes can be distinguished. Firstly, a constitutive $Ca^{2+}$/calmodulin-dependent NO synthase, which occurs, for example, in the endothelium and in the brain and liberates NO at these sites in response to certain stimuli and serves to regulate blood pressure and platelet function as well as cerebral functions. Secondly, an inducible $Ca^{2+}$-independent NO synthase, which occurs in a plurality of cells, such as, for example, in the smooth musculature, and in macrophages or hepatocytes. The latter can be induced by endotoxin and by cytokines and then liberates large quantities of NO over a long period of time.

This NO is cytotoxic for tumour cells and for microorganisms and is also responsible for serious diseases. Pathological decrease in blood pressure, for example in association with septic or haemorrhagic shock, tissue damage and inflammatory processes may be mentioned in this connection. However, NO produced by the inducible NO synthase also plays an important role in the genesis and course of Type 1 diabetes and in atherosclerosis. In addition to this, a high concentration of NO can damage DNA by deaminating cytosine.

WO 93/13055 has already disclosed that certain compounds which are derived from arginine are inhibitors of the inducible NO synthase.

Coumarins are pharmacologically active compounds whose vasodilatory effect, especially on the coronary arteries, has long been known and is described, for example, in DE-C 1 210 883, DE-C 1 246 754, DE-C 1 259 349, DE-A 1 668 877, DE-A 1 962 154 or DE-A 2 247 691. In addition to this, the effectiveness of the coumarin derivative chloricromene against an endotoxin-induced shock in rats is described in European Journal of Pharmacology 210 (1992), 107–113.

It has now been found, surprisingly, that coumarins inhibit the liberation of NO and are consequently outstandingly suitable for use in the prevention and control of disorders which result from an excessively high systemic level of NO or excessively high local concentrations of NO.

The present invention consequently relates to the use of coumarins of the general formula I

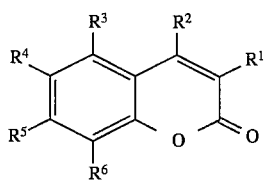

(I)

in which $R^1$ denotes hydrogen; halogen; $(C_2–C_6)$-alkenyl; $(C_7–C_{10})$-aralkyl; phenyl which is optionally substituted by $(C_1–C_4)$-alkyl, $(C_1–C_4)$-alkoxy, halogen, nitro or amino; $(C_1–C_6)$-alkyl, hydroxy-$(C_1–C_6)$-alkyl or dihydroxy-$(C_1–C_6)$-alkyl, which are optionally substituted by $(C_1–C_4)$-alkoxy, $(C_1–C_4)$-alkoxycarbonyl, $(C_1–C_4)$-alkylcarbonyl, amino or aminocarbonyl which can also be N-substituted or di-N-substituted,

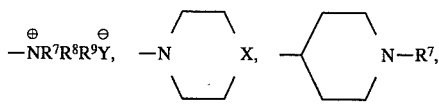

pyridyl or di-$(C_1–C_4)$-alkylamino-$(C_1–C_4)$-alkylthio; —CH(CH$_2$—NR$^7$R$^8$)$_2$; or di-$(C_1–C_4)$-alkylamino-$(C_1–C_4)$-alkylthio;

$R^2$ denotes $(C_1–C_6)$-alkyl which is optionally substituted by

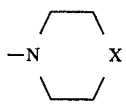

or amino or aminocarbonyl which can also be N-substituted or di-N-substituted; $(C_2–C_6)$-alkenyl; $(C_6–C_{10})$-aryl; or pyridyl;

$R^3$ and $R^4$, independently of each other, denote hydrogen; hydroxyl; $(C_1–C_4)$-alkoxy, hydroxy-$(C_1–C_4)$-alkoxy or dihydroxy-$(C_1–C_4)$-alkoxy which are optionally substituted by $(C_1–C_4)$-alkoxycarbonyl, amino or aminocarbonyl which can also be N-substituted or di-N-substituted, or

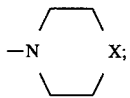

$(C_2–C_6)$-alkenyloxy; amino-$(C_1–C_4)$-alkyl which can also be N-substituted or di-N-substituted;

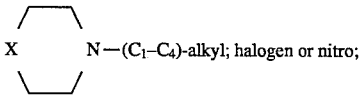

$R^5$ is defined as $R^3$ and additionally also denotes $CF_3$; $OR^7$; $(C_7–C_{10})$-aralkoxy; $(C_1–C_4)$-alkoxy which can be substituted by one or two hydroxyl groups or by

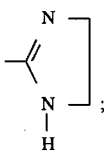

$(C_1–C_6)$-alkoxy which is substituted by —COOR$^7$ or —NR$^7$R$^8$; $(C_1–C_4)$-alkylcarbonyl; $(C_2–C_6)$-alkynyl; $(C_1–C_4)$-alkoxycarbonyloxy; NH$_2$; or NHR$^{10}$;

$R^6$ is defined as $R^5$ but cannot represent chlorine, $R^7$ denotes hydrogen; $(C_1–C_6)$-alkyl, hydroxy-$(C_1–C_6)$-alkyl or di-hydroxy-$(C_1–C_6)$-alkyl which are optionally substituted by amino, di-$(C_1–C_4)$-alkylamino, $(C_1–C_4)$-alkoxy, cyano,

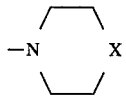

or a radical $R^{10}$; $(C_2–C_6)$-alkenyl; or $(C_7–C_{10})$-aralkyl;

$R^8$ denotes hydrogen; $(C_1-C_6)$-alkyl; $(C_1-C_4)$-alkoxy-$(C_1-C_6)$-alkyl; or $(C_7-C_{10})$-aralkyl;

$R^9$ denotes $(C_1-C_4)$-alkyl;

$R^{10}$ denotes aminocarbonyl; N-$(C_1-C_4)$-alkylaminocarbonyl; di-N-$(C_1-C_4)$-alkylaminocarbonyl; N-$(C_6-C_{10})$-arylaminocarbonyl;

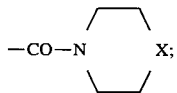

$(C_1-C_4)$-alkylcarbonyl; $(C_6-C_{10})$-arylcarbonyl; di-N-$(C_1-C_4)$-alkylaminomethylcarbonyl; —$SO_2(C_1-C_4)$-alkyl or —$SO_2(C_6-C_{10})$-aryl;

X denotes a single bond; O; $CH_2$; S; NH; N$(C_1-C_4)$-alkyl; N$(C_6-C_{10})$-aryl; or N(hydroxy-$(C_1-C_6)$-alkyl); and Y denotes Cl; Br; I; TosO; $HSO_4$ or $CH_3COO$, as well as their pharmacologically acceptable acid addition compounds, for controlling and preventing disorders which arise as the result of an elevated NO level.

$(C_1-C_4)$-Alkyl groups can be straight-chain or branched and denote, for example, methyl, ethyl, n-propyl, i-propyl, n-butyl, i-butyl, sec-butyl or tert-butyl. The same also applies to $(C_1-C_6)$ groups, which can additionally denote n-pentyl or n-hexyl, for example. This also applies in each case, in a corresponding manner, to alkoxy, alkylcarbonyl, alkylamino or alkylthio groups.

$(C_2-C_6)$-Alkenyl groups and $(C_2-C_6)$-alkynyl groups can also be straight-chain or branched. Examples of alkenyl groups are vinyl and allyl. An example of an alkynyl group is ethynyl.

$(C_6-C_{10})$-Aralkyl is, in particular, benzyl or phenethyl. $(C_6-C_{10})$-Aryl is, in particular, phenyl.

Halogen can represent fluorine, chlorine, bromine or iodine, with chlorine and bromine being preferred.

Amino or aminocarbonyl, which can also be N-substituted and di-N-substituted, have, in particular, the formulae —$NR^7R^8$ and —$CONR^7R^8$, respectively, with $R^7$ and $R^8$ being defined as indicated above.

The pyrrolidinyl residue, the morpholino residue, the 1,4-thiazinyl residue, the piperazinyl residue and the piperidinyl residue, for example, come within the formula

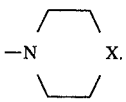

$R^1$ preferably denotes $(C_1-C_6)$-alkyl, di-$(C_1-C_4)$-alkylamino-$(C_1-C_6)$-alkyl and 3-di-$(C_1-C_4)$-alkylamino-2-hydroxypropyl. The diethylaminoethyl radical is particularly preferred.

$R^2$ preferably denotes $(C_1-C_6)$-alkyl or phenyl. Methyl is particularly preferred.

$R^3$ and $R^4$ preferably denote, independently of each other, $(C_1-C_4)$-alkoxy and by $NR^7R^8$-substituted ethoxy. Methoxy and hydrogen are particularly preferred for $R^3$ and hydrogen for $R^4$.

$R^5$ preferably denotes hydroxyl, methoxy, $(C_1-C_4)$-alkoxycarbonylmethoxy, aminocarbonylmethoxy, di$(C_1-C_4)$-alkylamino-$(C_1-C_4)$-alkoxy and amino-$(C_1-C_4)$-alkoxy.

$R^6$ preferably denotes hydrogen, hydroxyl, $(C_1-C_4)$-alkoxy, nitro and di-$(C_1-C_4)$-alkylamino-$(C_1-C_4)$-alkoxy.

The compounds of the general formula I are known and may be prepared by known methods (see, for example, Elderfield, Heterocyclic Compounds Vol.2, 173–216, (1951) and the patent literature cited above), for example by Pechmann's Coumarin Synthesis.

Compounds of the general formula I according to the invention which contain a basic group can form salts with inorganic or organic acids. Examples of suitable acids for the formation of pharmacologically acceptable acid addition salts are: hydrochloric, hydrobromic, naphthalenedisulphonic acids, in particular naphthalenedisulphonic acid(1,5), and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acids. The acid addition salts can be prepared, as is customary, by combining the components, expediently in a suitable solvent or diluent.

Disorders which arise as a result of an elevated NO level, and which consequently can be treated according to the invention with the compounds of the general formula I, or can be prevented with these compounds, are, in particular, pathological decreases in blood pressure, as occur in association with septic or haemorrhagic shock, in association with tumour therapy using cytokines, or in association with liver cirrhosis. Further examples are inflammatory diseases, such as rheumatoid arthritis and, in particular, ulcerative colitis, and also insulin-dependent diabetes mellitus and transplant rejection reactions.

The following diseases are also associated with an increased production of nitrogen monoxide and can be treated or prevented in accordance with the invention. In the heart/circulation sphere, these are arteriosclerosis, post-ischaemic tissue damage, reperfusion damage, myocarditis following infection with coxsackie virus, and cardiomyopathy; in the central nervous system sphere, forms of neuritis, encephalomyelites, viral neurodegenerative diseases, Alzheimer's disease, hyperalgesia, epilepsy and migraine; in the kidney sphere, acute kidney failure and glomerulonephritis.

Treatments in the stomach and uterus/placenta spheres are also conceivable, as is affecting the motility of sperm.

The inhibition by the compounds of the general formula I of NO release can be determined as follows by measuring NO using oxyhaemoglobin on macrophages:

Mouse macrophages (MM) from strain RAW 264.7 are cultured in petri dishes (10 cm diameter). DMEM (from Sigma, No. D 5405), conditioned with 4 mM L-glutamine, 3.5 g of D-glucose/l, 50 U/50 µg/ml pen/strep and 10% FCS, is employed as the nutrient medium, at 37° C., under 10% $CO_2$ and at an atmospheric humidity of 95%. The subconfluent cells are scraped off with a cell scraper and taken up in medium; the number of cells is determined (counting in 0.2% trypan blue solution) and the cells are sown out in 24-well plates ($0.5 \times 10^6$ cells/ml, 1 ml/well).

Approximately 18 hours after they have been sown out, the mouse macrophages, which have adhered well, are stimulated with LPS (Lipopolysaccharide from E. coli, Serotype 0111B4, from Sigma, No. L 2630) and γIFN (mouse recombinant, from Boehringer Mannheim, No. 1276905). For this purpose, the culture medium is sucked off from the cells and 1 ml of incubation medium (MEM; without phenol (Biochrome F0385), conditioned with 4 mM glutamine, 3.5 g of glucose/l, 3.7 g of $NaHCO_3$/l, 110 mg of Na pyruvate/l, 50 U/50 µg/ml pen/strep and 5% FCS) is added per well (24-well plate). 1 µl of LPS and 1 µl of γIFN are pipetted into each well.

As a result, the stimulators have the following concentrations:

140 ng of LPS/ml+5 U of γIFN/ml

Fresh synthesis of the NO-producing enzyme NO synthase (iNOS) is induced during the stimulation, which lasts for 4 hours. After this period of incubation, the incubation medium is sucked off and each well is rinsed twice with fresh incubation medium. Experimental medium (consisting of the incubation medium to which SOD, 30 U/ml, catalase, 290 U/ml, indomethacin, 3.5 μg/ml, oxyHb, approximately 8 μm, and test substance (100,500 μM) have been added) is added to the wells (1 ml/well for a 24-well plate). For the control, it is only the solvent of the test substance which is added to the conditioned experimental medium. The plates provided with experimental medium are incubated for 120 minutes in an incubator at 37° C., 10% $CO_2$ and 95% atmospheric humidity. After the 120-minute incubation, the experimental medium is pipetted into plastic semimicrocuvettes and the extinction difference 576–592 nm is measured on a DU 70.

Two wells are in each case loaded with one test substance (n=2), and one unstimulated control, one stimulation control and one positive control (nitro-L-arginine, 500 μM) are compared with the test substances on each plate. In order to measure the activity of the test substances, the extinction difference 576–592 nm is compared with that of the stimulation control and expressed in the form of a percentage. The extinction difference 576–592 nm for the experimental medium to which test substance has been added is measured at time point 0, as are the pH and osmolality of this medium.

After the experimental medium has been pipetted off, the cytotoxicity of the test substance is examined (viability with time, DNA synthesis).

Using this method, it was observed that carbocromene ($R^1$=diethylaminoethyl, $R^2$=methyl, $R^5$=ethoxycarbonylmethoxy $R^3$, $R^4$ and $R^6$=hydrogen or hydrochloride) in a quantity of 250 μM inhibits the release of NO from mouse macrophages by from 85 to 100% both in the induction phase and following stimulation with LPS/γ-IFN.

The effect of the compounds of the general formula I on blood pressure can be determined in the following in vivo experiment:

Firstly, male Sprague Dawley rats (from 280 to 440 g) are generally anaesthetized by being injected intraperitoneally with sodium pentobarbital (from 60 to 100 mg/kg). Once the rats are anaesthetized, they are tracheotomized and the animals are given artificial respiration using ambient air (from 10 to 13 ml $kg^{-1}$) at 54 inspirations/min. Subsequently, the peripheral veins (jugular vein and femoral veins) are exposed and catheters for the intravenous administration of test substances and for removing blood are inserted and secured. A catheter is inserted into the left carotid artery, and secured, and connected to a pressure sensor (type P23 Dd, Statham, Hato Ray, Puerto Rico). The systolic (BPs) and diastolic (BPd) blood pressures are recorded using a Brush Mark 220 polygraph.

At the end of an experiment (after 90 min), the rats are exsanguinated, and the plasma is isolated. The concentration of nitrite ($NO_2^-$) in the plasma is determined using the Griess Reaction.

Four groups containing four individual animals in each case were made up for carrying out this experiment using carbocromene. Group 1 was given sodium chloride (0.3 ml), group 2 carbocromene at a concentration of 10 mg/kg, group 3 a bolus injection of lipopolysaccharide (LPS) (*E. coli*, serotype 127:B08, TCA extract, Sigma Deisenhofen) at a concentration of 15 mg/kg, and group 4 carbocromene and LPS, the carbocromene being administered 10 minutes before the LPS. All the substances were given intravenously.

The results are recorded in the following table:

| Group | | Blood pressure (mmHg) Time (min) | | | | | Concentration of $NO_2$ in the plasma (nmol/ml) |
|---|---|---|---|---|---|---|---|
| | | 0 | 15 | 30 | 60 | 90 | |
| 1 | BPs | 125 ± 5 | 125 ± 5 | 125 ± 3 | 130 ± 6 | 130 ± 3 | 4.5 |
|   | BPd | 95 ± 6 | 90 ± 6 | 85 ± 4 | 85 ± 5 | 85 ± 5 | |
| 2 | BPs | 125 ± 5 | 125 ± 5 | 125 ± 3 | 130 ± 6 | 130 ± 3 | 4.5 |
|   | Bpd | 95 ± 6 | 90 ± 6 | 85 ± 4 | 85 ± 5 | 85 ± 5 | |
| 3 | BPs | 125 ± 6 | 55 ± 6 | 75 ± 5 | 70 ± 4 | 50 ± 6 | 9.3 |
|   | BPd | 95 ± 7 | 30 ± 5 | 45 ± 6 | 35 ± 5 | 25 ± 5 | |
| 4 | BPs | 125 ± 6 | 120 ± 6 | 120 ± 5 | 110 ± 4 | 110 ± 6 | 4.9 |
|   | Bpd | 90 ± 5 | 75 ± 5 | 70 ± 6 | 70 ± 5 | 70 ± 6 | |

The compounds of the general formula I and their pharmacologically acceptable acid addition salts can be administered to humans as medicines either on their own, in mixtures with each other, or in the form of pharmaceutical preparations which permit enteral or parenteral use and which contain, as the active constituent, an effective dose of at least one compound of the general formula I, or of an acid addition salt thereof, in addition to customary, pharmaceutically acceptable, carrier substances and additives.

The medicines can be administered orally, for example in the form of pills, tablets, lacquered tablets, coated tablets, hard and soft gelatine capsules, solutions, syrups, emulsions or suspensions, or aerosol mixtures. However, the administration can also be effected rectally, for example in the form of suppositories, or parenterally, for example in the form of solutions for injection, or percutaneously, for example in the form of ointments or tinctures.

Pharmaceutically inert inorganic or organic carrier substances may be used for producing the pharmaceutical preparations. For example, lactose, corn starch, or derivatives thereof, talc, stearic acid, or its salts, etc., can be used for producing pills, tablets, coated tablets and hard gelatine capsules. Examples of carrier substances for soft gelatine capsules and suppositories are fats, waxes, semi-solid and liquid polyols, natural or hardened oils, etc. Water, sucrose, invert sugar, glucose, polyols, etc., are, for example, suitable for use as carrier substances for producing solutions and syrups. Water, alcohols, glycerol, polyols or vegetable oils, for example, are suitable for use as carrier substances for producing solutions for injection.

In addition to the active compounds and carrier substances, the pharmaceutical preparations may also contain additives, such as, for example, fillers, extenders, disintegrants, binding agents, glidants, wetting agents, stabilizers, emulsifiers, preservatives, sweeteners, colourants, flavourants, aromatizing agents and buffering substances, and also solvents or solubilizers or agents for achieving a depot effect, as well as salts for altering the osmotic pressure, finishing agents or antioxidants. They may also contain two or more compounds of the general formula I or their pharmacologically acceptable acid addition salts and other therapeutically active substances in addition.

Examples of other therapeutically active substances of this nature are: β-receptor blockers, such as, for example, propranolol, pindolol and metoprolol; vasodilators, such as, for example, carbocromene; sedatives, such as, for example, barbituric acid derivatives, 1,4-benzodiazepine and meprobamate; diuretics, such as, for example, chlorothiazide; cardiotonics, such as, for example, digitalis preparations; anti-hypertensives, such as, for example, hydralazine, dihydralazine, ramipril, prazosin, clonidine and Rauwolfia alkaloids; agents which lower the level of fatty acids in the blood, such as, for example, bezafibrate and fenofibrate; and agents for thrombosis prophylaxis, such as, for example, phenprocoumon.

The dosage can vary within wide limits and is to be matched in each separate case to the individual circumstances. In general, a daily dose of from about 0.5 to 100 mg, preferably of from 1 to 20 mg, is appropriate for oral administration to a human patient. Owing to the fact that the active compounds are readily absorbed, the quantity required for the daily dose is similar for other forms of administration, i.e. in general also from 0.5 to 100 mg/patient. The daily dose is normally divided up into several, for example from 2 to 4, smaller doses which are administered separately.

| Example | R¹ | R² | R³ | R⁴ | R⁵ | R⁶ | m.p. | (°C.) |
|---|---|---|---|---|---|---|---|---|
| 1 | —CH₂CH₂NEt₂ | CH₃ | H | H | —OCH₂COOEt | H | .HCl | 156 |
| 2 | —CH₂CH₂—N(piperidine) | CH₃ | H | H | —OCH₂COOEt | H | .HCl | 209 |
| 3 | —CH₂CH₂NEt₂ | Ph | H | H | —OCH₂COOEt | H | HCl | 160 |
| 4 | —CH₂CH₂—N(morpholine) | CH₃ | H | H | —OCH₂COOEt | H | HCl | 205 |
| 5 | —CH₂CH₂—N(piperidine) | CH₃ | H | H | —OCH₂CH=CH₂ | H | HCl | 256 |
| 6 | —CH₂CH₂NEt₂ | CH₃ | H | H | —OEt | H | .HCl | 222 |
| 7 | —CH₂CH₂NEt₂ | CH₃ | H | H | —OC₄H₉ | H | .HCl | 287 |
| 8 | —(CH₂)₃NMe₂ | CH₃ | OH | H | —OH | H | .HCl | 233 |
| 9 | —CH₂CH₂—N(pyrrolidine) | CH₃ | H | H | —OH | H | HCl | 261 |
| 10 | —Ph | CH₃ | H | H | —OCH₂CH₂NEt₂ | H | | 47–50 |
| 11 | —C₄H₉ | CH₃ | H | H | —OCH₂CH₂NEt₂ | H | | 48 |
| 12 | —CH₂CO₂Et | CH₃ | H | H | —OH | CH₂NMe₂ | | 288 |
| 13 | —C₄H₉ | Ph | H | H | —OH | H | | 205 |
| 14 | —Et | CH₃ | H | H | —OCH₂CO₂oPr | H | .HCl | 125 |
| 15 | —CH₂Ph | CH₃ | H | H | —OCH₂CO₂tert.Bu | H | | 126 |
| 16 | —CH(CH₂NEt)₂ | CH₃ | H | H | —OCH₂CO₂Et | H | .HCl | 176 |

-continued

| | R¹ | R² | R³ | R⁴ | R⁵ | R⁶ | | m.p. |
|---|---|---|---|---|---|---|---|---|
| 17 | —CH₂CH₂—N(piperidinyl) | Ph | H | H | —O(CH₂)₃CH₃ | H | | 242 |
| 18 | —CH₂CH₂NEt₂ | CH₃ | H | H | —OCH₂Ph | H | | 92 |
| 19 | —CH₂CH₂NEt₂ | CH₃ | H | H | —OCH₂—C(=O)—CH₃ | H | | 142 |
| 20 | —CH₂CH₂NEt₂ | CH₃ | H | H | —OCH₂CONMe₂ | H | .HCl | 206 |
| 21 | —CH₂CH₂NEt₂ | CH₃ | H | H | —OCH₂—C(=O)—NBu₂ | H | .HCl | 130 |
| 22 | —CH₂CH₂NEt₂ | CH₃ | H | H | —OCH₂CON(piperidinyl) | H | | 121 |
| 23 | —CH₂CH₂NEt₂ | CH₃ | H | H | —OCH₂—C(=O)—NHBu | H | | 129 |
| 24 | —CH₂CH₂NEt₂ | CH₃ | H | H | —OCH₂—C(=O)—NHEt | H | | 125 |
| 25 | —CH₂CH₂NEt₂ | CH₃ | H | H | —OCH₂CO₂iPr | H | .HCl | 136 |
| 26 | —CH₂CH₂NEt₂ | CH₃ | H | H | —OCH₂CO₂CH₂CH(CH₃)₂ | H | .HCl | 72 |
| 27 | —CH₂CH₂NEt₂ | CH₃ | H | H | —OCH₂CO₂tert.Bu | H | .HCl | 204 |
| 28 | —CH₂CH₂NEt₂ | CH₃ | H | H | —OCH₂CONH(CH₂)₂NH₂ | H | | 116–118 |
| 29 | —CH₂CH₂NEt₂ | CH₃ | H | H | —OCH₂CONH(CH₂)₂NH—C(=O)—CH₃ | H | | 193 |
| 30 | —CH₂CH₂NEt₂ | CH₃ | H | H | —OCH₂CONH(CH₂)₃NMe₂ | H | | 126 |
| 31 | —(CH₂)₂NEt₃⁺ Br⁻ | CH₃ | H | H | —OCH₂CO₂Et | H | | 92 |

-continued

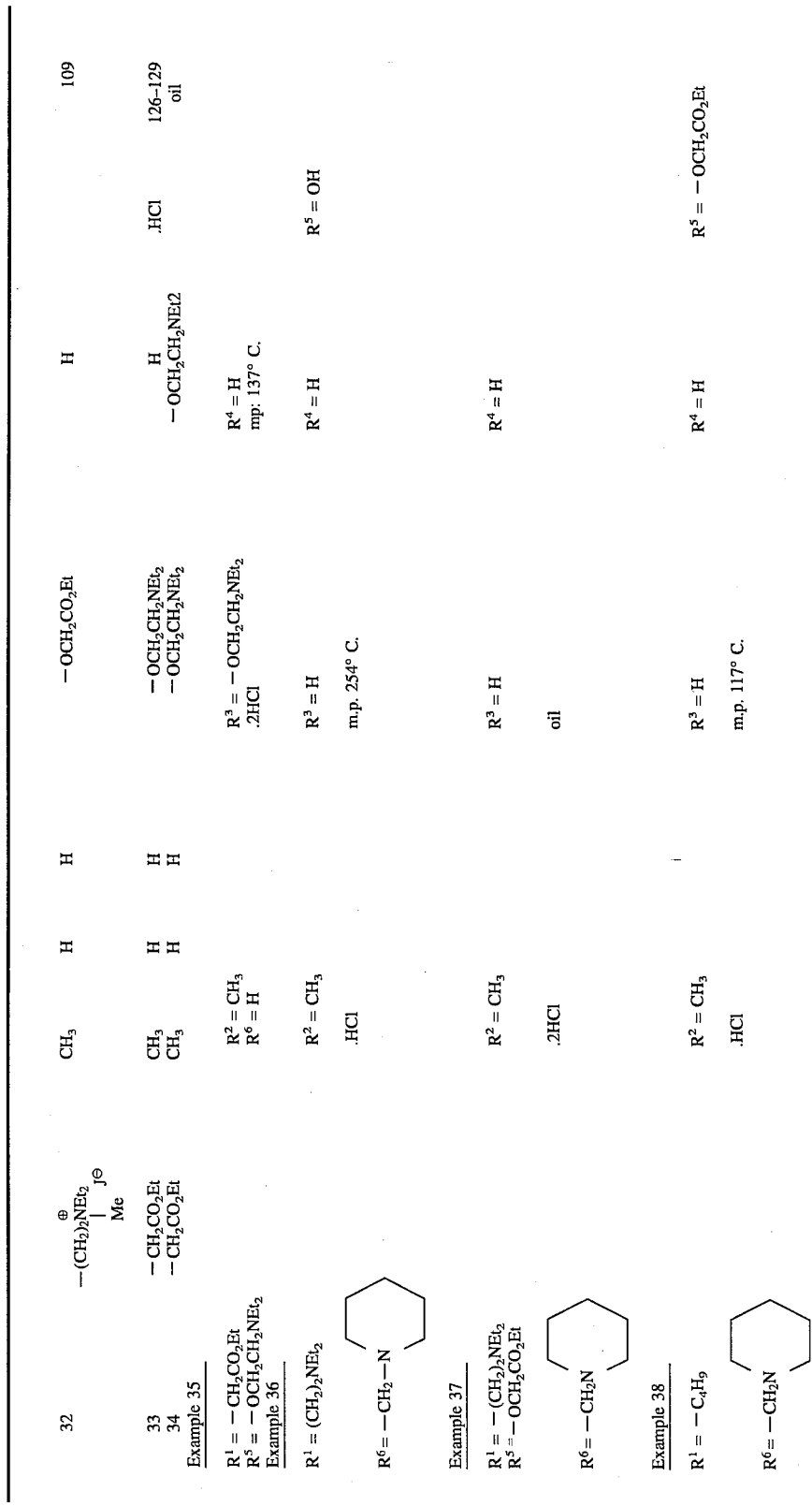

| | $R^1$ | $R^2$ | $R^3$ | | |
|---|---|---|---|---|---|
| 32 | —(CH$_2$)$_2$N$^⊕$Et$_2$ J$^⊖$ Me | CH$_3$ | H | H | —OCH$_2$CO$_2$Et | 109 |
| 33 | —CH$_2$CO$_2$Et | CH$_3$ | H | H | —OCH$_2$CH$_2$NEt$_2$ | 126–129 |
| 34 | —CH$_2$CO$_2$Et | CH$_3$ | H | H | —OCH$_2$CH$_2$NEt$_2$ | oil |

Example 35
$R^1$ = —CH$_2$CO$_2$Et
$R^5$ = —OCH$_2$CH$_2$NEt$_2$
$R^3$ = —OCH$_2$CH$_2$NEt$_2$  .2HCl Example 36
$R^1$ = —(CH$_2$)$_2$NEt$_2$  $R^2$ = CH$_3$  $R^3$ = H  $R^4$ = H
$R^6$ = —CH$_2$—N⟨piperidine⟩  .HCl  mp: 137° C.

$R^3$ = H  $R^4$ = H  $R^5$ = OH
m.p. 254° C.

Example 37
$R^1$ = —(CH$_2$)$_2$NEt$_2$  $R^2$ = CH$_3$  $R^3$ = H  $R^4$ = H
$R^5$ = —OCH$_2$CO$_2$Et
$R^6$ = —CH$_2$N⟨piperidine⟩  .2HCl  oil Example 38
$R^1$ = —C$_4$H$_9$  $R^2$ = CH$_3$  $R^3$ = H  $R^4$ = H  $R^5$ = —OCH$_2$CO$_2$Et
$R^6$ = —CH$_2$N⟨piperidine⟩  .HCl  m.p. 117° C.

-continued

[Structure: chromen-2-one with R¹ at 3-position, R² at 4-position, R³, R⁴, R⁵, R⁶ on benzene ring]

Example 39

$R^1 = -CH_2CONH(CH_2)_3N\text{(piperidinyl)}$; $R^2 = Me$; $R^3 = H$ $R^4 = H$; $R^5 = OH$; $R^6 = H$; m.p. 255° C.

Example 40

$R^1 = -CH_2CONH(CH_2)_2NEt_2$; $R^2 = CH_3$; $R^3 = H$; $R^4 = H$ $R^5 = -OCH_2CO_2Et$; $R^6 = H$; .HCl; m.p 143° C.

Example 41

$R^1 = -CH_2CONH(CH_2)_2NEt_2$; $R^2 = -CH_2CONH(CH_2)_2NEt_2$; $R^3 = H$; $R^4 = H$ $R^5 = OH$; $R^6 = H$; oil

Example 42

$R^1 = H$; $R^2 = -CH_2N\text{(morpholinyl)}$; $R^3 = H$; $R^4 = H$ $R^5 = -OCH_2CO_2Et$; $R^6 = H$; m.p. 150° C.

Example 43

$R^1 = -CH_2CH_2NEt_2$; $R^2 = CH_3$; $R^3 = H$; $R^4 = H$; m.p. 125° C.

$R^5 = -OCH_2CO_2Et$; $R^6 = -C(=O)-CH_3$

Example 44

$R^1 = -CH_2CH_2NEt_2$; $R^2 = CH_3$; $R^3 = H$; $R^4 = H$; m.p. 229° C.

$R^5 = -OMe$; $R^6 = H$; .HCl

Example 45

$R^1 = -CH_2CH_2NEt_2$; $R^2 = CH_3$; $R^3 = H$; $R^4 = H$

-continued

[Structure: chromone-type with R¹, R² on pyranone ring; R³, R⁴, R⁵, R⁶ on benzene ring]

| | | | |
|---|---|---|---|
| R⁵ = —OCHCO₂Et<br>         \|<br>         CH₃ | R⁶ = H | | m.p. 131° C. |

Example 46

| | | | |
|---|---|---|---|
| R¹ = —CH₂CH₂NEt₂<br>R⁵ = —OCH₂CH₂CO₂Et | R² = CH₃<br>R⁶ = H | R³ = H<br>.HCl | R⁴ = H<br>m.p. 167° C. |

Example 47

| | | | |
|---|---|---|---|
| R¹ = —CH₂CH₂NEt₂<br>R⁵ = —OCH₂CH₂CN | R² = CH₃<br>R⁶ = H | R³ = H<br>.HCl | R⁴ = H<br>m.p. 210° C. |

Example 48

| | | | |
|---|---|---|---|
| R¹ = —CH₂CH₂NEt₂<br>R⁵ = —OCH₂CONHCH₂CH₂OH | R² = CH₃<br>R⁶ = H | R³ = H<br>.HCl | R⁴ = H<br>m.p. 168° C. |

Example 49

| | | | |
|---|---|---|---|
| R¹ = —CH₂CH₂NEt₂ | R² = CH₃<br>R⁶ = H | R³ = H<br>.HCl | R⁴ = H |
| R⁵ = —O—C—CO₂Et<br>         / \\<br>        CH₃  CH₃ | | | m.p. 127° C. |

Example 50

| | | | |
|---|---|---|---|
| R¹ = —CH₂CH₂NEt₂<br>R⁵ = —O(CH₂)₂NEt₂ | R² = CH₃<br>R⁶ = H | R³ = H<br>.2HCl | R⁴ = H<br>m.p. 254° C. |

Example 51

| | | | |
|---|---|---|---|
| R¹ = —CH₂CH₂NEt₂<br>R⁵ = —OCH₂CO₂H | R² = CH₃<br>R⁶ = H | R³ = H<br>.HCl | R⁴ = H |

Example 52

| | | | |
|---|---|---|---|
| R¹ = —CH₂CH₂NEt₂<br>R⁵ = —OCH₂CO₂Et | R² = CH₃<br>R⁶ = —NO₂ | R³ = H<br>.HCl | R⁴ = H<br>m.p. 198° C. |

Example 53

| | | | |
|---|---|---|---|
| R¹ = —CH₂CH₂NEt₂<br>R⁵ = —OCH₂CO₂Et | R² = CH₃<br>R⁶ = —NH₂ | R³ = H<br>.2HCl | R⁴ = H<br>m.p. 188° C. |

Example 54

| | | | |
|---|---|---|---|
| R¹ = —CH₂CH₂NEt₂<br>R⁵ = —OCH₂CO₂Et | R² = CH₃<br>R⁶ = H | R³ = H<br>.HCl | R⁴ = Cl<br>m.p. 211° C. |

-continued

[Structure: coumarin with R¹, R², R³, R⁴, R⁵, R⁶ substituents]

| Example | Substituents | | |
|---|---|---|---|
| Example 55 | R¹ = H<br>R⁵ = OCH₂CO₂Et | R² = 4-pyridyl<br>R⁶ = H | R³ = H<br>.HCl | R⁴ = H<br>m.p. 206° C. |
| Example 56 | R¹ = H<br>R⁵ = —OCH₂CO₂Et | R² = 3-Pyridyl<br>R⁶ = H | R³ = H<br>.HCl | R⁴ = H<br>m.p. 189° C. |
| Example 57 | R¹ = —(CH₂)₂NEt₂<br>R⁵ = —OCH₂CONH₂ | R² = Me<br>R⁶ = H | R³ = —OCH₂CONH₂<br>m.p. 236° C. | R⁴ = H |
| Example 58 | R¹ = —S—(CH₂)₂NEt₂<br>R⁵ = —OCH₂CHCH₂ | R² = CH₃<br>R⁶ = H | R³ = H<br>.HCl | R⁴ = H<br>m.p. 153° C. |
| Example 59 | R¹ = (CH₂)₂N⟨piperazine⟩N(CH₂)₂OH | R² = CH₃ | R₃ = H | R₄ = H |
| | R⁵ = —OCH₂CO₂Et | R⁶ = H | .2HCl | m.p. 212° C. |
| Example 60 | R¹ = —(CH₂)₂N⟨piperazine⟩N—Me | R² = CH₃ | R³ = H | R⁴ = H |
| | R⁵ = —OCH₂CO₂Et | R⁶ = H | .2HCl | m.p. 241° C. |
| Example 61 | R¹ = —(CH₂)₂N⟨thiomorpholine⟩S | R² = H | R³ = H | R⁴ H |
| | R⁵ = —OCH₂CO₂Et | R⁶ = H | .HCl | m.p. 226° C. |

-continued

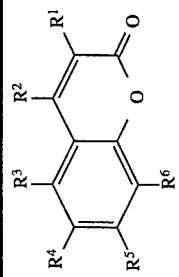

| | | | |
|---|---|---|---|
| Example 62 | | | |
| $R^1 = -(CH_2)_2NEt_2$ | $R^2 = CH_3$ | $R^3 = H$ | $R^4 = -OCH_2CO_2Et$ |
| $R^5 = -OCH_2CO_2Et$ | $R^6 = H$ | .HCl | m.p. 184° C. |
| Example 63 | | | |
| $R^1 = -CH_2CHCH_2-NH$<br>            |<br>            OH 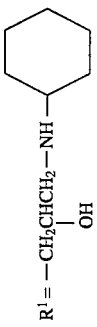 | $R^2 = CH_3$ | $R^3 = H$ | $R^4 = H$ |
| $R^5 = -OCH_2CO_2Et$ | $R^6 = H$ | .HCl | m.p. 208–209° C. |
| Example 64 | | | |
| $R^1 = -CH_2CHCH_2-NH$<br>            |<br>            OH 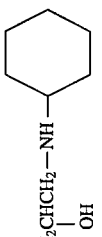 | $R^2 = CH_3$ | $R^3 = H$ | $R^4 = H$ |
| $R^5 = -HO$ | $R^6 = H$ | .HCl | m.p. 266° C. |
| Example 65 | | | |
| $R^1 = -CH_2CHCH_2NH(CH_2)_3OMe$<br>           |<br>           OH | $R^2 = CH_3$ | $R^3 = H$ | $R^4 = H$ |
| $R^5 = -OCH_2CO_2Et$ | $R^6 = H$ | .HCl | m.p. 179° C. |
| Example 66 | | | |
| $R^1 = -CH_2CHCH_2N$ 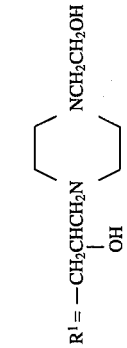 $NCH_2CH_2OH$ | $R^2 = CH_3$ | $R^3 = H$ | $R^4 = H$ |
| $R^5 = -OMe$ | $R^6 = -OMe$ | .2HCl | m.p. 240° C. |
| Example 67 | | | |
| $R^1 = H$ | $R^2 = Ph$ | $R^3 = H$ | $R^4 = H$ |

-continued structure: coumarin-like with R1, R2 on the pyranone and R3, R4, R5, R6 on the benzene ring

| | | | |
|---|---|---|---|
| R⁵= —OCH₂CHCH₂NHiPr<br>　　　　　　\|<br>　　　　　　OH | R⁶ = H | | m.p. 183–185° C. .HCl |

Example 68

| | | | |
|---|---|---|---|
| R¹ = Bu | R² = Me | R³ = H | R⁴ = H |
| R⁵= —OCH₂CHCH₂NHiPr<br>　　　　　　\|<br>　　　　　　OH | R⁶ = H | .HCl | m.p. 169–170° C. |

Example 69

| | | | |
|---|---|---|---|
| R¹ = —CH₂CH₂—⟨N⟩—N(CH₂)₂OH | R² = CH₃ | R³ = H | R⁴ = H |
| R⁵= —OCH₂CHCH₂—N⟨N⟩—NCH₂CHOH<br>　　　　　　\|　　　　　　　　　\|<br>　　　　　　OH　　　　　　　　　CH₃ | R⁶ = H | .2HCl | m.p. 222° C. |

Example 70

| | | | |
|---|---|---|---|
| R¹ = Bu | R² = —(CH₂)₂CH₃ | R³ = H | R⁴ = H |
| R⁵= —O(CH₂)₃N⟨N⟩—NCH₂CHOH<br>　　　　　　　　　　　　　　　　　\|<br>　　　　　　　　　　　　　　　　CH₃ | R⁶ = H | .2HCl | | m.p. 215–217° C.

Example 71

| | | |
|---|---|---|
| R¹ = —(CH₂)₂—⟨N⟩—N(CH₂)₄OH | R² = —(CH₂)₂CH₃ | |
| R³ = H | R⁴ = H | R⁵ = OCH₃　　R⁶ = OCH₃　　.2HCl | m.p. 200–203° C.

-continued

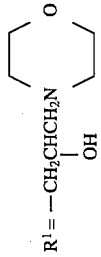

| Example 72 | | |
|---|---|---|
| $R^1 = -CH_2CH-CH_2N$ 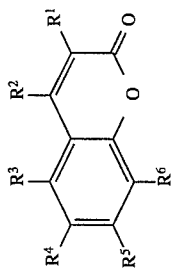 $NCH_2CHOH$ $CH_3$ $\|$ $OH$ | | |
| $R^2 = Ph$ .2HCl | $R^3 = H$ m.p. 224–225° C. | $R^4 = OCH_3$ $R^5 = OCH_3$ $R^6 = H$ |
| Example 73 | | |
| $R^1 = -CH_2CH_2N(CH_2)_2OH$ $\|$ $CH_3$ | | |
| $R^2 = CH_3$ $R^6 = H$ | $R^3 = OMe$ m.p. 87° C. | $R^4 = H$ $R^5 = OMe$ |
| Example 74 | | |
| $R^1 = -CH_2CONH(CH_2)_3NEt_2$ $R^5 = OMe$ | $R^2 = CH_3$ $R^6 = H$ .2HCl | $R^3 = H$ $R^4 = OMe$ m.p. 208° C. |
| $R^1 = -(CH_2)_2NEt_2$ $R^5 = -O(CH_2)_2N(CH_2)_2OH$ $\|$ $Me$ | $R^2 = CH_3$ $R^6 = H$ .2HCl | $R^3 = H$ $R^4 = H$ m.p. 195° C. |
| Example 76 | | |
| $R^1 = -CH_2CHCH_2N$ 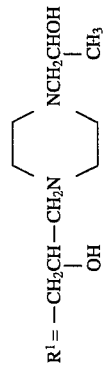 $O$ $\|$ $OH$ | | |
| $R^2 = CH_3$ .HCl | $R^3 = OMe$ m.p. 80° C. | $R^4 = OMe$ $R^5 = OMe$ $R^6 = H$ |

-continued

[Structure: coumarin core with R¹ at 3-position, R² at 4-position, R³, R⁴, R⁵, R⁶ on benzene ring, lactone C=O and O]

| Example | | | | | |
|---|---|---|---|---|---|
| Example 77 | | | | | |
| R¹ = —CH₂CHCH₂N(C₃H₇)₂<br>                │<br>                OH | R² = Ph<br>.HCl | R³ = H<br>m.p. 60° C. | | | |
| Example 78 | | | | | |
| R¹ = —CH₂CH=CH₂ | R² = CH₃<br>m.p. 110° C. | R⁴ = Br | R⁵ = OMe | R⁶ = OMe | |
| R⁶ = —OCH₂—CH—CH₂<br>              │   │<br>              OH  NH<br>                   │<br>                   CH(CH₃)₂ | R² = CH₃ | R³ = H | R⁴ = H | | |
| Example 79 | | | | | |
| R¹ = H | R⁵ = H | R³ = OCH₂CHCH₂NHiPr<br>               │<br>               OH | | | |
| R⁴ = H | | R⁶ = H<br>.2HCl | .HCl | m.p. 205° C. | |
| Example 80 | | | | | |
| R¹ = —(CH₂)₂NEt₂ | R² = CH₃ | R³ = H | R⁴ = H<br>m.p. 188° C. | | |
| R⁵ = —OCH₂CHCH₃<br>             │<br>             NH₂ | R⁶ = H | | | | |
| Example 81 | | | | | |
| R¹ = —(CH₂)₂NEt₂ | R² = CH₃<br>.HCl | R³ = H<br>m.p. 180° C. | R⁴ = H | R⁵ = OEt | |
| R⁵ = —NH—C—N⟨morpholine⟩<br>         ‖<br>         O | | | | | |

-continued
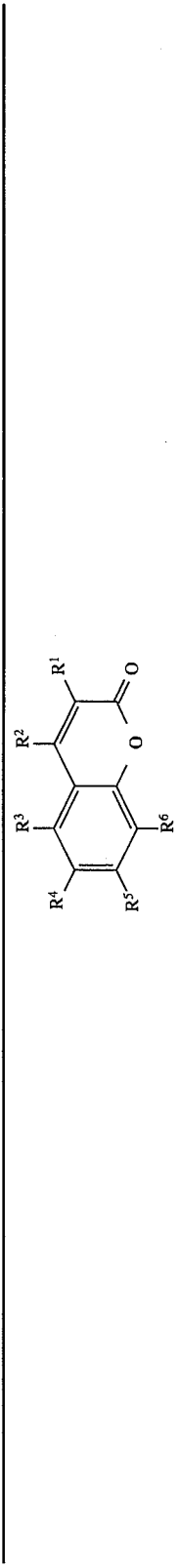
| | | | |
|---|---|---|---|
| Example 82 | | | |
| R¹ = —(CH₂)₂NEt₂ | R² = CH₃ | R³ = H | R⁴ = H |
| R⁵ = —NHCO₂Et | R⁶ = H | .HCl | m.p. 244–246° C. |
| Example 83 | | | |
| R¹ = —(CH₂)₂NEt₂ | R² = CH₃ | R³ = H | R⁴ = H |
| R⁵ = 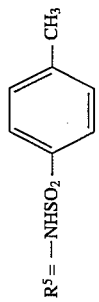 | R⁶ = H | .HCl | m.p. 230° C. |
| Example 84 | | | |
| R¹ = —(CH₂)₂NEt₂ | R² = CH₃ | R³ = H | R⁴ = H |
| R⁵ = 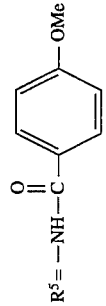 | R⁶ = H | m.p. 230° C. (acetate) | |
| Example 85 | | | |
| R¹ = —(CH₂)₂NEt₂ | R² = CH₃ | R³ = H | R⁴ = H |
| R⁵ = —NHCH₂CO₂Et | R⁶ = H | .HCl | m.p. 196° C. |
| Example 86 | | | |
| R¹ = —CH₂CONH(CH₂)₂NEt₂ | R² = CH₃ | R³ = H | R⁴ = H |
| R⁵ = 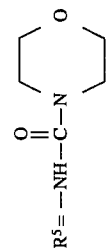 | R⁶ = H | .HCl | m.p. 170° C. |
| Example 87 | | | |
| R¹ = —(CH₂)₂NEt₂ | R² = CH₃ | R³ = H | R⁴ = H |

-continued

[Structure: phenyl ring with R³, R⁴, R⁵, R⁶ substituents connected to C=C(R²)(R¹)–C(=O)–O forming a chromone/coumarin-like core]

| | | | |
|---|---|---|---|
| R⁵ = —NHCOCH₂N(morpholine) | .HCl | m.p. 158–160° C. | |
| Example 88 | | | |
| R¹ = —(CH₂)₂N(morpholine) | R² = CH₃ | R³ = H | R⁴ = H |
| R⁵ = —NH—C(=O)—NH₂ | R⁶ = H | .HCl | m.p. 308–310° C. decomp. |
| Example 89 | | | |
| R¹ = —(CH₂)₂N(morpholine) | R² = CH₃ | R³ = H | R⁴ = H |
| R⁵ = —NH—C(=O)—NHEt | R⁶ = H | m.p. 264–266° C. | |
| Example 90 | | | |
| R¹ = —(CH₂)₂N(morpholine) | R² = CH₃ | R³ = H | R⁴ = H |
| R⁵ = —NHCONEt₂ | R⁶ = H | m.p. 215–217° C. | |

-continued
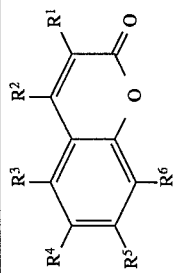
| Example | | | | |
|---|---|---|---|---|
| Example 91 | | | | |
| $R^1 = -(CH_2)_2N$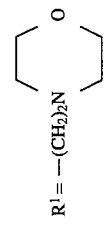 | $R^2 = CH_3$ | $R^3 = H$ | $R^4 = H$ | |
| $R^5 = -NHCON$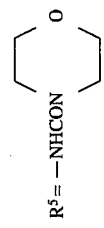 | $R^6 = H$ | .HCl | | m.p. 292–294° C. |
| Example 92 | | | | |
| $R^1$ = Pyrid-3-yl | $R^2 = H$ | $R^3 = H$ | $R^4 = H$ | |
| $R^5 = O-CH_2-CO_2Et$ | $R^6 = H$ | m.p.: 158–161° C. | | |
| Example 93 | | | | |
| $R^1 = H$ | $R^2 = CH_3$ | $R^3, R^4 = H$ | $R^5 = NEt_2$ | |
| $R^6 = H$ | m.p.: 72–75° C. | | | |
| Example 94 | | | | |
| $R^1 = CH_2CH_2-NEt_2$ | $R^2 = CH_3$ | $R^3, R^4 = H$ | | |
| $R^5 = NH-CONHCO_2Et$ | $R^6 = H$ | .HCl | | |
| | 193° C. decomp. | | | |

We claim:

1. Method for treating a host afflicted with an excessively high NO level, against disorders which arise as the result of an elevated NO level in the body which comprises administering to such a host in need thereof an effective dose of a coumarin compound of the formula I

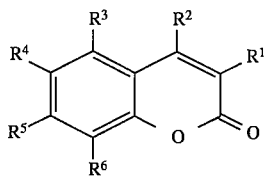

in which

R$^1$ denotes hydrogen; halogen; (C$_2$–C$_6$)-alkenyl; (C$_7$–C$_{10}$)-aralkyl; phenyl which is optionally substituted by (C$_1$–C$_4$)-alkyl, (C$_1$–C$_4$)-alkoxy, halogen, nitro or amino; (C$_1$–C$_6$)-alkyl, hydroxy-(C$_1$–C$_6$)-alkyl or dihydroxy-(C$_1$–C$_6$)-alkyl, which are optionally substituted by (C$_1$–C$_4$)-alkoxy, (C$_1$–C$_4$)-alkoxycarbonyl, (C$_1$–C$_4$)-alkyl-carbonyl, amino or aminocarbonyl which can also be N-substituted or di-N-substituted.

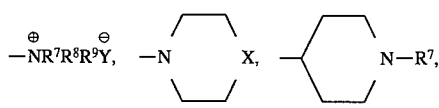

pyridyl or di-(C$_1$–C$_4$)-alkylamino-(C$_1$–C$_4$)-alkylthio; —CH(CH$_2$—NR$^7$R$^8$)$_2$; or di-(C$_1$–C$_4$)-alkylamino-(C$_1$–C$_4$)-alkylthio; R$^2$ denotes (C$_1$–C$_6$)-alkyl which is optionally substituted by

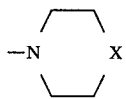

or amino or aminocarbonyl which can also be N-substituted or di-N-substituted; (C$_2$–C$_6$)-alkenyl; (C$_6$–C$_{10}$)-aryl; or pyridyl;

R$^3$ and R$^4$, independently of each other, denote hydrogen; hydroxyl; (C$_1$–C$_4$)-alkoxy, hydroxy-(C$_1$–C$_4$)-alkoxy or dihydroxy-(C$_1$–C$_4$)-alkoxy which are optionally substituted by (C$_1$–C$_4$)-alkoxycarbonyl, amino or aminocarbonyl which can also be N-substituted or di-N-substituted, or

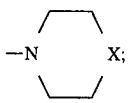

(C$_2$–C$_6$)-alkenyloxy; amino-(C$_1$–C$_4$)-alkyl which can also be N-substituted or di-N-substituted;

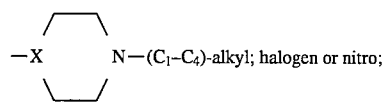

R$^5$ is defined as R$^3$ and additionally also denotes CF$_3$; OR$^7$; (C$_7$–C$_{10}$)-aralkoxy; (C$_1$–C$_4$)-alkoxy which can be substituted by one or two hydroxyl groups or by

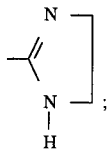

(C$_1$–C$_6$)-alkoxy which is substituted by —COOR$^7$ or —NR$^7$R$^8$; (C$_1$–C$_4$)-alkylcarbonyl; (C$_2$–C$_6$)-alkynyl; (C$_1$–C$_4$-alkoxycarbonyloxy; NH$_2$; or NHR$^{10}$; R$^6$ is defined as R$^5$ but cannot represent chlorine; R$^7$ denotes hydrogen; (C$_1$–C$_6$)-alkyl, hydroxy-(C$_1$–C$_6$)-alkyl or dihydroxy-(C$_1$–C$_6$)-alkyl which are optionally substituted by amino, di-(C$_1$–C$_4$)-alkylamino, (C$_1$–C$_4$)-alkoxy, cyano,

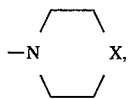

or a radical R$^{10}$, (C$_2$–C$_6$)-alkenyl; or (C$_7$–C$_{10}$)-aralkyl; R$^8$ denotes hydrogen; (C$_1$–C$_6$)-alkyl; (C$_1$–C$_4$)-alkoxy-(C$_1$–C$_6$)-alkyl; or (C$_7$–C$_{10}$)-aralkyl; R$^9$ denotes (C$_1$–C$_4$)-alkyl; R$^{10}$ denotes aminocarbonyl; N-(C$_1$–C$_4$)-alkylaminocarbonyl); di-N-(C$_1$–C$_4$)-alkylaminocarbonyl; N-(C$_6$–C$_{10}$)-arylaminocarbonyl;

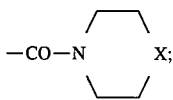

(C$_1$–C$_4$)-alkylcarbonyl; (C$_6$–C$_{10}$)-arylcarbonyl; di-N-(C$_1$–C$_4$)-alkylaminomethylcarbonyl; —SO$_2$(C$_1$–C$_4$)-alkyl or —SO$_2$(C$_6$–C$_{10}$)-aryl; X denotes a single bond; O; CH$_2$; S; NH; N(C$_1$–C$_4$)-alkyl; N(C$_6$–C$_{10}$)-aryl; or N(hydroxy-(C$_1$–C$_6$)-alkyl; and Y denotes Cl; BR; I; TosO; HSO$_4$ or CH$_3$COO, and their pharmacologically acceptable acid addition compounds.

2. Method according to claim 1, characterized in that R$^1$ denotes (C$_1$–C$_6$)-alkyl, di-(C$_1$–C$_4$)-alkylamino-(C$_1$–C$_6$)-alkyl,

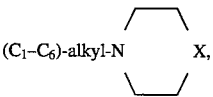

or 3-di-(C$_1$–C$_4$)-alkylamino-2-hydroxypropyl.

3. Method according to claim 1, characterized in that R$^2$ denotes methyl.

4. Method according to claim 1, characterized in that R$^3$ and R$^4$, independently of each other, denote (C$_1$–C$_4$)-alkoxy or NR$^7$R$^8$-substituted ethoxy.

5. Method according to claim 1, characterized in that $R^5$ denotes hydroxyl, methoxy, $(C_1-C_4)$-alkoxycarbonylmethyoxy, di-$(C_1-C_4)$-dialkylaminocarbonylamino,

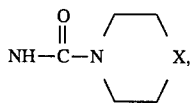

or amino-$(C_1-C_4)$-alkoxy.

6. Method according to claim 1, characterized in that $R^6$ denotes hydrogen, hydroxyl, $(C_1-C_4)$-alkoxy, nitro or di-$(C_1-C_4)$-alkylamino-$(C_1-C_4)$-alkoxy.

7. Method according to claim 1 in which said disorder is one which produces pathological decreases in blood pressure.

8. Method according to claim 1 in which said disorder is one which produces ulcerative colitis.

9. Method according to claim 1 in which said disorder is one which produces septic shock.

10. Method according to claim 1 in which said disorder is one which produces transplant rejection reactions.

* * * * *